United States Patent
Joseph (10) Patent No.: US 10,675,011 B2
(45) Date of Patent: Jun. 9, 2020

(54) SAFETY ISOLATION BAGS FOR INTRA ABDOMINAL, ENDOSCOPIC PROCEDURES, POWER MORCELLATION AND VAGINAL MORCELLATION

(71) Applicant: Lalu Joseph, Kerala State (IN)

(72) Inventor: Lalu Joseph, Kerala State (IN)

( * ) Notice: Subject to any disclaimer, the term of this patent is extended or adjusted under 35 U.S.C. 154(b) by 328 days.

(21) Appl. No.: 15/524,558

(22) PCT Filed: Nov. 12, 2015

(86) PCT No.: PCT/IN2015/000420
§ 371 (c)(1),
(2) Date: May 4, 2017

(87) PCT Pub. No.: WO2016/079752
PCT Pub. Date: May 26, 2016

(65) Prior Publication Data
US 2018/0008250 A1    Jan. 11, 2018

(30) Foreign Application Priority Data
Nov. 19, 2014 (IN) .......................... 5813/CHE/2014

(51) Int. Cl.
*A61B 17/00* (2006.01)
*A61B 17/34* (2006.01)
(Continued)

(52) U.S. Cl.
CPC .... *A61B 17/00234* (2013.01); *A61B 17/3474* (2013.01); *A61B 90/90* (2016.02);
(Continued)

(58) Field of Classification Search
CPC .. A61B 2017/00287; A61B 2017/2212; A61B 2017/2215; A61B 2017/2217;
(Continued)

(56) References Cited

U.S. PATENT DOCUMENTS 5,176,687 A    1/1993    Hasson et al. ................ 606/114
5,524,633 A    6/1996    Heaven et al. ............... 128/749
(Continued)

FOREIGN PATENT DOCUMENTS

WO    WO 13/75103    5/2013    ............. A61B 17/00

OTHER PUBLICATIONS

International Search Report, PCT Application No. PCT/IN2015/000420, pp. 1-3 (dated Apr. 21, 2016).

*Primary Examiner* — Katherine H Schwiker
(74) *Attorney, Agent, or Firm* — J. Peter Paredes; Rosenbaum IP, P.C.

(57) ABSTRACT

A safety isolation bag is a pneumoperitoneum device for intra-abdominal, endoscopic procedures, power morcellation and vaginal morcellation for facilitating safe removal of body mass from within the abdominal cavity. It comprises of an expandable and collapsible enclosed internal space (5) having a neck portion (4) with mouth (3) having retractor means (2) and provided with markings, colour coded indicating how much the bag is to be pulled out for the removal of large, medium and small tissue mass, and also having one or more non-return valves (6) attached with long looped threads (8) on one of the surface in the wall of the safety isolation bag below the neck as a means for introducing the surgical instruments and accessories into the enclosed internal space at the right place and to close the puncture hole after the procedure. It is made of one or more layers of flexible biocompatible/medical grade plastic film.

10 Claims, 6 Drawing Sheets

(51) Int. Cl.
- *A61B 90/90* (2016.01)
- *A61B 90/92* (2016.01)
- *A61B 17/221* (2006.01)
- *A61B 90/00* (2016.01)
- *A61B 90/40* (2016.01)
- *A61B 17/02* (2006.01)
- *A61B 17/32* (2006.01)

(52) U.S. Cl.
CPC ............ *A61B 90/92* (2016.02); *A61B 17/221* (2013.01); *A61B 17/32002* (2013.01); *A61B 90/40* (2016.02); *A61B 2017/00287* (2013.01); *A61B 2017/00557* (2013.01); *A61B 2017/0225* (2013.01); *A61B 2017/2212* (2013.01); *A61B 2017/320024* (2013.01); *A61B 2090/063* (2016.02); *A61B 2090/0807* (2016.02); *A61B 2217/005* (2013.01); *A61B 2217/007* (2013.01)

(58) Field of Classification Search
CPC ....... A61B 2017/320024; A61B 2017/320028; A61B 2017/320032; A61B 2017/00557; A61B 2017/0225; A61B 2017/3425; A61B 2017/3427; A61B 2017/3429; A61B 2017/22035; A61B 2017/22037; A61B 2017/4216; A61B 2017/320064; A61B 17/00234; A61B 17/221; A61B 17/32002; A61B 17/0218; A61B 17/3423; A61B 17/22031; A61B 17/48; A61B 90/92; A61B 90/40; A61B 2090/401; A61B 46/13; A61B 46/17; A61B 2050/314; A61B 2050/316; A61B 2050/318; A61B 10/06

See application file for complete search history.

(56) References Cited

U.S. PATENT DOCUMENTS

| | | | |
|---|---|---|---|
| 6,685,628 B2 | 2/2004 | Vu | 600/37 |
| 7,547,310 B2 | 6/2009 | Whitfield | 600/114 |
| 7,955,292 B2* | 6/2011 | Leroy | A61B 17/00234 206/216 |
| 8,585,712 B2 | 11/2013 | O'Prey et al. | A61B 17/22 |
| 2006/0025654 A1 | 2/2006 | Suzuki et al. | 600/114 |
| 2011/0190781 A1* | 8/2011 | Collier | A61B 17/00234 606/114 |
| 2013/0184536 A1 | 7/2013 | Shibley et al. | A61B 17/0218 |
| 2014/0236168 A1 | 8/2014 | Shibley et al. | A61B 17/00234 |
| 2014/0330285 A1* | 11/2014 | Rosenblatt | A61B 17/42 606/114 |
| 2015/0320409 A1* | 11/2015 | Lehmann | A61B 17/221 600/109 |
| 2016/0302783 A1* | 10/2016 | Greenberg | A61B 17/00234 |
| 2017/0231611 A1* | 8/2017 | Holsten | A61B 1/3132 606/114 |
| 2017/0252026 A1* | 9/2017 | Gupta | A61B 17/00234 |

\* cited by examiner

SAFETY ISOLATION BAGS FOR INTRA ABDOMINAL, ENDOSCOPIC PROCEDURES, POWER MORCELLATION AND VAGINAL MORCELLATION

TECHNICAL FIELD

The present disclosure generally relates to "safety isolation bag", a pneumoperitoneum device for intra-abdominal, endoscopic procedures, power morcellation and vaginal morcellation and more especially meant for total laparoscopic hysterectomy (TLH), laparoscopy assisted vaginal hysterectomies, laparoscopic myomectomies and other endoscopic procedures where benign or malignant tissues have to be removed. More especially it relates to safety isolation bag having one or more layered wall provided with soft and flexible non-return valves made of biocompatible/medical grade plastic material for the insertion of instruments during laparoscopic surgery. Further said non-return valves are attached with tubular guides and long looped threads to help to guide and puncture the bag in suitable position of the valves as well as to close the puncture hole after the procedure by pulling the thread.

BACKGROUND OF THE ART

Laparoscopic morcellation is commonly used in surgeries to remove bulky specimens from the abdomen using minimally invasive techniques. Historically, morcellation was performed using a device that required the surgeon or assistant to manually 'squeeze' the handle. Other reports describe using a scalpel directly through the abdomen to create small specimens that can be drawn out of the abdominal cavity. Power Morcellation is associated with spreading of cellular material of the morcellated tissues.

Hence using an isolation bag during morcellation is one of the options in minimally invasive endoscopic surgeries. Morcellation within an insufflated isolation bag is a feasible technique and methods for morcellating uterine tissue in a contained manner may provide an option to minimize the risks of open power morcellation while preserving the benefits of minimally invasive surgery. It is also reported that the patients who underwent endometrial morcellation, using a normal isolation bag, during minimally invasive hysterectomy or myomectomy, the possibility of spread of tissue beyond the isolation bag and additional punctures to the bag during the procedure cannot be ruled out causing postoperative pain, infection and the potential to spread undetected malignancy.

Hence the quality and the design of the isolation bag is of paramount importance as during the procedure it could result in tiny punctures in the bag or could spread microscopic cells beyond the bag.

A number of patents are there related to "safety isolation bags" for intra abdominal, endoscopic procedures, power morcellation and vaginal morcellation. In this connection U.S. Pat. Nos. 5,176,687; 5,524,633 A (WO1995009666A1); US 20130184536 A1; U.S. Pat. Nos. 6,685,628 B2; 7,547,310 B2; and 8,585,712 B2 are mentioned here by way of reference. One of the drawbacks of the prior art patents is that it requires more number of steps in introducing the bag and instrumentation as well as for the retrieval of the specimen. In addition, this causes enhanced procedural time. Further learning curve associated with other isolation bags appears to be very high as it involves complicated steps in comparison with the safety isolation bag of the present invention. The procedural outcome also is not evident in the similar bags used for laparoscopic surgery.

None of the prior art patents has any similarity with the features of the safety isolation bag disclosed according to the present invention. According to other prior art technologies/products that are similar to the invention are endo bags with two tail openings, endo bags with one opening, normal plastic bags, urinal bags etc. (traditional methods). Recently even the USFDA has given a strict warning on using power morcellation. Hence doctors are scared and are trying to use different models of bags like urine bags or simple plastic bags for placing the surgical specimen for morcellation. Therefore, there is a need for an alternate easy and safe solution for power morcellation and tissue removal. Hence to overcome the above drawbacks, I have come out with a state of the art safety isolation bag with better safety features and ease of utilizing in laparoscopic procedures. The safety isolation bag according to the present disclosure will offer a great solution for the same. At present most of such procedures are done without using any safety devices or bags.

OBJECTIVES OF THE PRESENT INVENTION

The main objective of the present invention is to provide an isolation bag for intra-abdominal, endoscopic procedures, power morcellation and vaginal morcellation which is very safe, avoiding spillage of fine tissue pieces and body fluids during surgery to remove bulky specimens from the abdomen, using minimally invasive techniques including during gynecologic surgery.

One more objective of the present invention is to have multiple incision endoscopic procedures making the procedure simple, safe and avoid complicated steps which are there in case of bags with multi tail end-openings.

Yet another objective of the present invention is to have an isolation bag which once inflated will get filled completely inside the abdominal cavity keeping away all organs from the field of morcellation or tissue extraction.

Still another objective of the invention is to have an isolation bag which can withstand and reduce the chances of accidental puncture while in use during the procedure.

One more objective of the invention is to doubly ensure that the bag does not leak during the laparoscopic procedure, by providing multi-walled construction of the bag.

Yet another objective of the invention is to have provisions like primary instrument insertion sleeve attached to the inner side of the bag at the mouth and provided with an inlet opening for introducing telescope, and other apparatus such as trocar, morcellator/cutting instrument, suction apparatus etc. required for power morcellation, extraction of the body mass and also for inflating the bag to create peritoneum especially during single incision laparoscopic surgeries.

Still another objective of the invention is to provide 1 or more soft and flexible non-return valves along the walls on the upper side of the safety isolation bag attached with long looped thread, for introducing telescope, and other apparatus such as trocar, morcellator/cutting instrument, suction apparatus etc. required for power morcellation, extraction of the body mass and also for inflating the bag to create pneumoperitoneum and to prevent gas leakage as most of the endoscopic procedures use multiple instruments from multiple body sites.

Another objective of the invention is to provide a long looped thread to the non-return valve to help to puncture the safety isolation bag in the right position and to give counter pressure while puncturing to insert the trocars, in addition to closing the puncture hole completely by pulling said thread after completing the tissue mass removal.

One more objective of the invention is to provide one or more tubular guides attached at the non-return valves to guide the trocars directly to the valves and puncture the safety isolation bag at the proper place.

Yet another objective of the invention is to provide two 20 to 30 cm long threads attached at both sides of the opening of the safety isolation bag to facilitate to keep open the bag during the removal of dermoid cyst from the ovary.

SUMMARY OF THE INVENTION

According to the invention, the safety isolation bag, a pneumoperitoneum device for intra-abdominal, endoscopic procedures, power morcellation and vaginal morcellation for facilitating the safe removal of a mass from within the abdominal or body cavity is inflatable and having single or multilayered walls made out of flexible medical grade plastic, preferably having two layered walls.

It is having a neck portion with a mouth or a wide opening. It is preferred to have a retainer ring which is flexible to keep the bag in open condition and to facilitate entry through an incision as well as for introducing surgical instruments and accessories and also to close the bag by pulling the retainer ring/thread. The ring can be of a springy material such as an engineering polymer, stainless steel, nickel titanium super elastic alloy, or elastomer or non elastic thread. It is even possible to do the procedure without having such retainer ring for the safety isolation bag. Said neck portion is in communication with the enclosed internal space. The neck is having markings indicating how much the bag is to be pulled out for large, medium and small tissue mass removal. This enclosed space or enclosure can be of bulbous shape when inflated. The enclosed shape is formed from material selected from polyolefin, polyethylene terephthalate, polybutylene terephthalate, polyvinyl chloride, ionomer, polyurethane, nylon, polycarbonate, acrylic, ethylene vinyl acetate copolymer, polyvinylidene fluoride or blends thereof preferably from low density poly ethylene, poly urethane and poly propylene. Said bag is from one or more combination of process such as injection, blow or rotational molding, casting or dipping, radio frequency welding, or bonding or any other suitable method known to those skilled in the art. The material used has to be flexible, gas-impermeable, and biocompatible medical grade.

In a preferred embodiment under the invention it can be formed by welding or bonding flexible medical grade plastic film into bag shaped assembly with enclosed internal space or cavity having a neck portion with mouth or a wide opening, at one end thereof and welding or bonding is done throughout the circumferential sites distributed over the surface of the said plastic film.

A retractor means is attached to the periphery of the mouth of the bag which facilitates to pull out the bag through the incision made in the body once the tumor is placed inside the device. Even a non-traumatic grasper can be used for pulling out the bag, instead of retractor means.

Soft and flexible non-return valves are provided on one of the surfaces below the neck in one or more places for introducing the surgical instruments and accessories into the enclosed internal space or cavity and to prevent gas leakage during the surgery. Further these non-return valves are attached with long looped threads to facilitate the introduction of instruments at the right place in the wall, while said thread is kept pulled out of the body incision during the procedure.

In accordance with another embodiment under the invention one tubular guide is attached to each of the non return valves, in addition to long looped thread, to facilitate for the introduction of instruments at the right place in the wall, so as to guide the instruments when the safety isolation bag is punctured at the no return valve. This will prevent any accidental damage while passing the trocar to puncture the device and can also ensure that there will not be any accidental spillage if the trocar is withdrawn by mistake.

The safety isolation bag is introducible through any of the endoscopic incisions/vaginal incision and is capable of being pushed through the body incision by means of introducer/blunt obturator and the said bag defines an internal space in an expanded state for reception of the masses to be removed from the abdominal cavity and collapsible from its expanded state. The body mass removed from the body cavity is placed/directed through the mouth of the bag into the internal space defined by the said bag, after which the mouth of the bag is pulled using the retractor means or using a non-traumatic grasper till the specified marking on the neck of the bag comes out of the body incision, whereupon the escape of the body mass from the mouth of the bag is prevented. Provision exists for the surgical instruments and accessories to introduce through the mouth directly into the enclosed internal space or through the soft and flexible non-return valves.

According to another embodiment under the invention, the safety isolation bag is provided with two about 20 cm to 30 cm long threads attached at both the sides of the opening to facilitate to keep open the bag during the removal of dermoid cyst from the ovary.

In yet another embodiment under the invention, a primary instrument insertion sleeve is attached to the inner side of the bag at the mouth and provided with an inlet opening and outlet for the surgical instruments and accessories to introduce into the enclosed internal space or cavity.

A method of removing a mass from within a body cavity, using safety isolation bag according to a preferred embodiment under the invention comprise of the following steps:

a) insert the safety isolation bag into the abdominal cavity directly using the blunt obturator (10) by pushing the bag through one of the incision, once it is ready for the removal of the specimen/surgical mass using the power morcellation;

b) remove the obturator once it passes the safety isolation bag through the incision, while pulling the safety isolation bag fully into the abdominal cavity using the non-traumatic grasper (11) through the lateral port or incision, keeping the retractor means (2) outside the patient's incision/body, while being observed through the telescope (13), already inserted;

c) open the mouth of the bag using a non-traumatic grasper (11) through the lateral port and place the tissue specimens to be removed inside the safety isolation bag;

d) pull the mouth of the safety isolation bag out using the retractor means or using a non traumatic grasper (2) till the markings provided at the neck area of the bag depending on the size of the tissues or the abdominal cavity size of the patient;

e) pull out the long looped thread (8) attached to the non-return valve by means of non-traumatic grasper (11) through the lateral port where the primary trocar is placed and simultaneously withdraw the telescope and trocar out of the lateral incision;

f) inflate the safety isolation bag through the gas pipe connected to the trocar (12) which is passed through the mouth opening of the bag, so that the complete pneumoperitoneum is created covering the abdominal cavity which is well monitored using a telescope;

g) pull the long looped thread attached to the non-return valve to give counter pressure and puncture at the non-return valve and introduce a trocar while being visualized through the telescope.

h) Introduce another sharp trocar, if required, through the other non-return valve for introducing another hand instrument for the procedure. Get the internal view of the safety isolation bag by means of the telescope introduced through the trocar which is placed inside the bag through the non return valve;

i) tie the long looped thread attached to the non-return valve to the trocar or keep it tightly pulled with a grasper to prevent accidental slippage of the bag from the trocar;

j) remove the trocar (12) and telescope (13) which was inserted through the mouth of the safety isolation bag and use this opening to introduce the morcellator hand piece (15) through the wide mouth opening of the bag to the cavity by a clockwise spiral movement;

k) inflate the safety isolation bag again through the gas pipe (14) introduced through the primary trocar, once all the instruments are inserted, so that the complete pneumoperitoneum is created covering the abdominal cavity with the safety isolation bag and the internal organs are kept away from the field of morcellation;

l) visualize and monitor inside of the safety isolation bag, through the telescope (15) passed through the trocar (12) and connected to the monitor screen;

m) introduce the morcellator hand piece (cutter blade hand instrument) (15) into the safety isolation bag using a blunt tip obturator with a spiral inward movement under vision;

n) remove the blunt obturator from the morcellator hand piece (cutter blade) and pass a tenaculam (16) through the hand piece lumen and hold the specimen and perform the morcellation within the pneumoperitoneum created by the safety isolation bag;

o) extract the tissues, once the morcellation is completed, take out the tenaculam (16) and remove all body fluids (20) and small tissue pieces using a suction irrigation apparatus (17) which is passed through the same morcellator hand piece (15);

p) deflate the safety isolation bag by using the suction apparatus (17), which is passed through the morcellator hand piece and create vacuum;

q) remove the Trocar after untying the long looped thread of the non-return valve tied to the Trocar and pull the thread tightly so that the puncture hole is closed, and then pull out the safety isolation bag by pulling out the morcellator hand piece (15) and the safety isolation bag together.

According to another embodiment under the invention, where tubular guide is attached to the each of the non return valve, in addition to long looped thread, method of removing a mass from within a body cavity, using safety isolation bag said step e) and said step g) require following modified steps:

In step e) tubular guide (8a) is to be pulled out along with long looped thread (8) attached to the non-return valve by means of non-traumatic grasper (11);

Similarly in step g) closed tip of the tubular guide is cut and the trocar is introduced through the tubular guide before puncturing the non-return valve under vision.

BRIEF DESCRIPTION OF THE DRAWINGS

These objectives and other features, aspects, and advantages of the present invention will be better understood when the detailed description is read with reference to the following drawings according to a preferred embodiment under the invention.

Wherein

1—Enclosure or enclosed space of bulbous shaped multilayered bag assembly.
2—Retractor means.
3—Mouth/wide opening of safety isolation bag.
4—Neck portion of the safety isolation bag.
5—Cavity of safety isolation bag for collecting the specimen/body mass.
6—Soft and flexible non-return valve for easy insertion of the trocar and for preventing gas leakage.
6a—Opening of primary instrument insertion sleeve provided towards the distal end for introducing primary instrument.
6b—Outlet of the obliquely cut outlet of the primary instrument insertion sleeve for free movement of the instruments.
7—A flexible retainer ring embedded with double layered fold in the upper circumferential portion of the mouth of the safety isolation bag to keep the mouth opened automatically once it is released and also to close the device by pulling the retainer means/retainer thread to prevent slipping off the body mass from the device.
8—Long looped thread attached to the non-return valve.
8a—Tubular guide attached to the non-return valve for guiding the trocar to the right place in the non return valve
9—Long threads attached at both the sides of opening of the safety isolation bag.
10—Blunt obturator.
11—Non-traumatic grasper.
12—Trocar (5 mm/10 mm).
13—5 mm/10 mm telescope for internal view which is connected to the monitor screen.
14—Gas tubing to inflate the bag to create pneumoperitoneum.
15—Morcellator hand piece for morcellating (making into small pieces) the surgical mass.
16—Tenaculam (5 mm/10 mm) to hold the body mass tightly which is inserted through the morcellator hand piece while morcellation.
17—Suction apparatus (10 mm/5 mm) passed through the morcellator hand piece after the morcellation is completed to remove small pieces of tissues, body fluids and blood.
18—Hand instrument.
19—Tissue mass.
20—Small pieces of tissue and body fluids collected at the bottom of the bag.

DETAILED DESCRIPTION OF THE INVENTION

Features of the present invention will become apparent to those skilled in the art upon reading the following detailed description of the preferred embodiments under this Invention.

The safety isolation bag according to the present invention is for Intra abdominal, endoscopic procedures, power morcellation and vaginal morcellation, total laparoscopic hysterectomy (TLH), laparoscopy assisted vaginal hysterectomies, laparoscopic myomectomies and other endoscopic procedures for removing benign or malignant tissues. Intra-abdominal or vaginal uterus morcellation are well described and routinely practiced techniques in removing benign bulky uterus or fibroids. But the chances of developing cancer due to the spillage of malignant tissues are of utmost concern during such procedures. Since it is not very sure that the tissues to be removed are benign or malignant, the uterus or any such masses needs to be removed intact to avoid intra peritoneal spillage of the cancer cells. For safe power morcellation and during other situations where it is difficult to manage suspicious surgical specimens, they can be taken out during endoscopic procedures (intra-abdominal, endoscopic or vaginal procedures) through a safety isolation bag, either through the umbilicus incision or through any other lateral incision or through vaginal approach. This invention is intended to make power morcellation and other surgical specimen/tissue removal safer with less procedural steps, which not only saves surgery time, but also avoid related complications.

Figure 1:
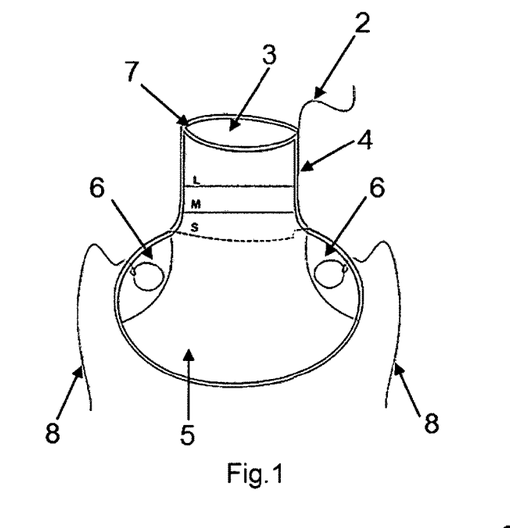
FIG. 1 shows safety isolation bag constructed of multi-layer with flexible non-return valves in two places attached with a long looped thread and colour coded which are at a distance of about 4 to 18 cm from the neck end of the safety isolation bag.

Referring to FIG. 1, safety isolation bag is an inflatable pneumoperitoneum device comprising of an expandable and collapsible enclosed internal space or cavity (5) bulbous in shape when inflated through gas tubing (14) and having a neck portion (4) with a mouth or a wide opening (3) made out of single layered or multilayered flexible gas-impermeable, biocompatible medical grade flexible material. According to a preferred embodiment under the invention the safety isolation bags is made of two layered construction. This will prevent significant level of gas leakage while directly puncturing the safety isolation bag with trocars or any other instruments during laparoscopic surgery once the pneumoperitoneum is created. It will help surgeons to use multiple ports on the anterior walls of the bag as per their choice for the easy handling of instruments and for perfect internal vision for morcellation or in any such safety isolation surgeries.

Further one or more number of non-return valves (6) are provided on one of the surface in the walls of the safety isolation bag below the neck as means for introducing the surgical instruments and accessories into the enclosed internal space or cavity (5) in multiple port surgeries for preventing gas leakage and to maintain the pneumoperitoneum. Said non-return valve is further attached with long looped threads (8) for using multiple instruments. These long looped threads help to puncture the bag at right position in the valves. By pulling the thread, it gives enough counter pressure for puncturing to insert the trocars. Once the procedure is done, the looped thread (8) is pulled tightly so that the puncture hole gets closed completely. Hence soft and flexible non-return valves with long looped threads can be provided on one of the surface of the bag below the neck in one or more places. These non-return valves are soft and flexible and made of biocompatible/medical grade plastic film and provided along the walls of the safety isolation bag for easy insertion of the trocar and for preventing gas leakage. The non-return valves are marked with colour codes for easy identification.

This bag can be made from one of the material selected from polyolefin, polyethylene terephthalate, polybutylene terephthalate, polyvinyl chloride, ionomer, polyurethane, nylon, polycarbonate, acrylic, ethylene vinyl acetate copolymer, polyvinylidene fluoride or blends thereof preferably from low density poly ethylene, poly urethane and poly propylene. This bag can be formed by injection, blow or rotational molding, dipping, casting or radio frequency welding or bonding, or any other suitable method known to those skilled in the art. In a preferred embodiment under the invention said bag can be formed by welding or bonding layer of flexible medical grade plastic film into bag shaped assembly (1) with enclosed internal space or cavity (5) having a neck portion (4) with mouth (3) or a wide opening, at one end thereof. Here bonding or welding is done throughout the circumferential sites distributed over the surface of the said plastic films. Mouth of the safety isolation bag is having a diameter of about 10 to 30 cm while total length of the safety isolation bag from the opening of the neck end to fundus which is the effective length inside the abdominal cavity, which is ranging from 15 to 40 cm and with a maximum width of about 15 to 45 cm. The neck portion (4) of the bag is having a length of about 5 to 15 cm. Markings are provided in the neck portion indicating how much the device can be pulled out viz., L—for the removal of large size tissue mass; M—for the removal of medium size tissue mass; S—for the removal of small tissue mass. The mouth of the bag is kept in open position by a flexible retainer ring element (7) embedded with double layered at the upper circumferential portion to facilitate entry for introducing surgical instruments and accessories. This arrangement facilitates to keep the mouth open automatically on applying pressure from sides and collapse on releasing pressure. Said retainer ring element is made out of a springy material such as an engineering polymer, stainless steel, nickel titanium super elastic alloy, elastomer or other elastic material. One retractor means (2) of about 30 to 55 cm length is attached to the mouth of the bag enabling to pull out the bag from the abdominal cavity through the body incision and is flexible. The retractor means can be in the form of a strip, tape or thread preferably made of the material of the isolation bag.

Figure 1A:
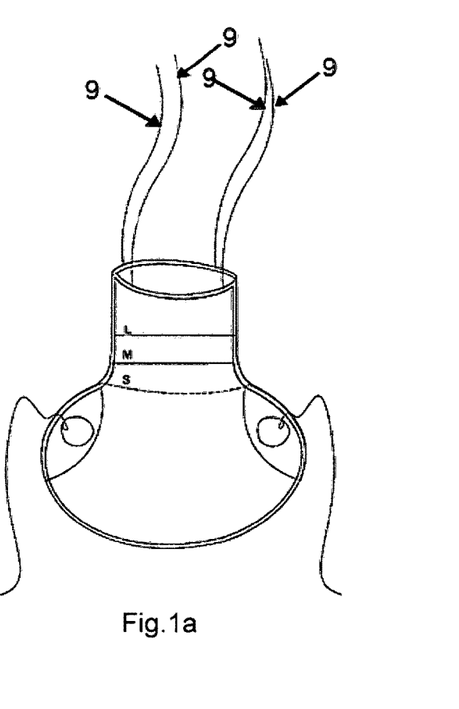
FIG. 1a shows the safety isolation bag additionally provided with two up to 30 cm long threads attached at both the sides of opening of the safety isolation bag to facilitate to use for dermoid cyst removal from the ovary.
Figure 1B:
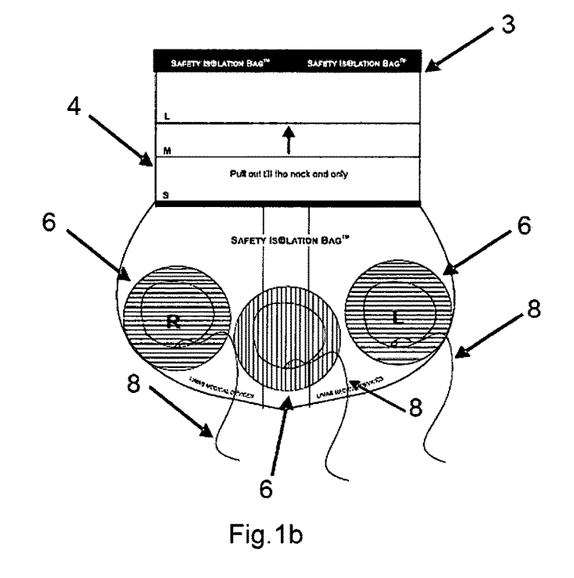
FIG. 1b shows one side of the safety isolation bag having 3 non-return valves provided on the surface and these are fixed with long looped threads according to one of the embodiment under the invention.
Figure 1C:
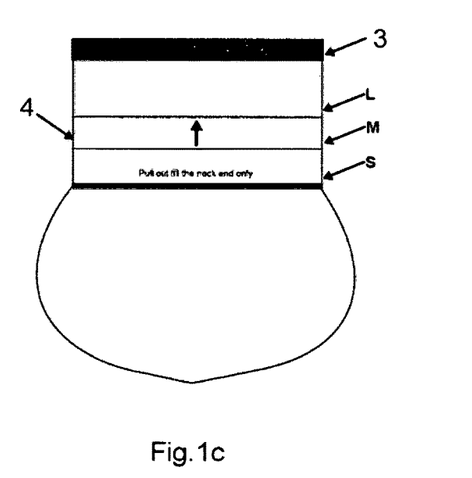
FIG. 1c shows the other side of the corresponding bag shown in FIG. 1b.
Figure 1D:
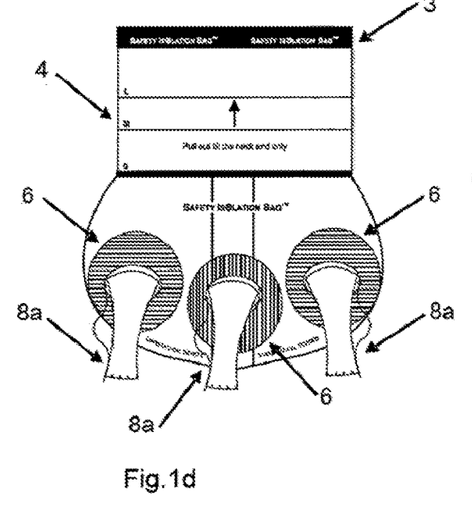
FIG. 1d shows the safety isolation bag provided with non return valves attached with long looped threads and the tubular guides for guiding the trocar to puncturing the safety isolation bag at right place in the non return valve.

In accordance with another embodiment under the invention one tubular guide (8a) is attached as shown in FIG. 1d to each of the non return valve, in addition to long looped threads, to facilitate for the introduction of instruments at the right place in the wall, so as to guide the instruments when the safety isolation bag is punctured at the no return valve. This will prevent any accidental damage while passing the trocar to puncture the device and can also ensure that there will not be any accidental spillage if the trocar is withdrawn by mistake.

Said tubular guide can be of same diameter at both ends or higher diameter at one end, which is attached to the non return valve in a sealing manner and is tapering towards the other end and that end will be closed. The tubular guide is of about 2 to 5 cm diameter with length up to 20 cm and is positioned on the non return valve in such a way that the long looped thread (8) is outside the base of the tubular guide (8a) The tubular guide along with the long looped thread is taken out of the incision/port made in the body by the surgeon for passing the trocars.

Once said tube is brought out, the tube is cut at the desired length making an opening through which trocars and other instruments are passed and punctured into the internal cavity of the safety isolation bag for morcellation of the tissue mass.

In a preferred embodiment under the invention, these non return valves are inbuilt on the anterior walls of the safety isolation bag by welding one or more additional layer over the bag at the earmarked portion of the anterior wall of the safety isolation bag at 4 cm to 25 cm distance from the end portion of the neck of the safety isolation bag. These multi layered wall of the bag on one of the surface in one or more location below the neck as shown in FIG. 1, FIG. 1a, FIG. 1b, FIG. 1c and FIG. 1d functions as non-return valve and allow the trocars to pierce the bag for other hand instruments to pass through without any gas leakage. This again enhances the free movement of the instruments without any hindrance on internal vision while using telescopes and instruments from multiple sites.

Figure 1E:
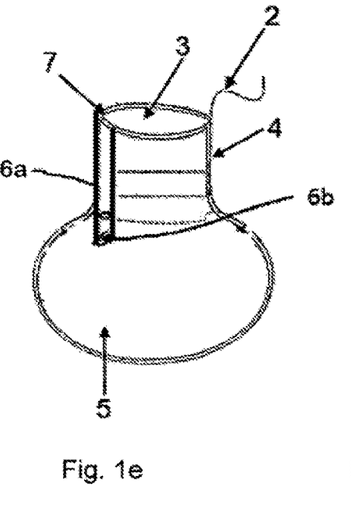
FIG. 1e shows the safety isolation bag provided with the primary instrument insertion sleeve attached to the inner side of the bag at the mouth with separate inlet opening instead of said no-return valves.

In another embodiment under the invention a primary instrument insertion sleeve (5) is attached to inner sidewall at the neck portion instead of non return valve. It is provided with an opening (6a) with a dia of 5 to 15 mm to pass the surgical instruments. Said opening is facing opposite to the inner wall of the neck portion to which sleeve is attached and towards the distal end of the sleeve. Outlet (6b) of the sleeve is provided with oblique cut for maximum movability of the instruments. In other words primary instrument insertion sleeve is having a length of about 20 cm at one side and 15 cm on the other side with inlet opening (6a) for inserting the primary instrument at 5 cm from the shorter length.

Safety isolation bag is inflatable and made out of single layer/multilayers of flexible medical grade plastic such as low density poly ethylene, poly urethane, poly propylene etc. and is also substantially transparent. It has sufficient strength and as such is very safe avoiding leakage during surgery while removing bulky specimens from the abdomen using minimally invasive techniques including during gynecologic surgery.

In addition to using the non-return valve with the looped thread, direct puncturing of the wall of the safety isolation bag with trocars can also be done, if required, for inserting the instruments such as morcellator hand piece without any leakage, once the safety bag is inflated covering the abdominal cavity as a pneumoperitoneum, because of the flexibility and elasticity of the material used for the construction of the walls.

In a preferred embodiment under the invention, the safety isolation bag can be made gas leak proof when punctured with surgical instruments like trocars even with single layered bag by welding one or two additional layers over the said single walled bag at the earmarked portion of the anterior wall of the safety isolation bag, which can function as non-return valve when surgical instruments penetrates the bag in-situ during the surgery. But care should be taken to select the right material of the bag.

Figure 2:
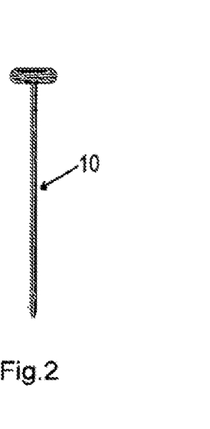
FIG. 2 shows blunt tip obturator of 5-10 mm diameter with a length of 25 to 35 cm for inserting the safety isolation bag into the abdominal cavity through any of the incisions.

The safety isolation bag according to my invention is made to shrink or collapse for inserting into the abdominal cavity through one of the abdominal incisions viz. the umbilicus incision/supra-umbilicus incision/lateral incision/vaginal incision by means of a blunt tip obturator made out of plastic as shown in FIG. 2. It is further pushed through using the same blunt tip obturator, once the body mass or surgical specimen is ready for removal. The obturator is having about 5 to 10 mm diameter and 25 to 35 cm length. According to the present invention, there is no necessity of using washers for making it leak proof while introducing both the trocar and morcellator hand piece.

The safety isolation bag according to the invention defines an internal space in an expanded state for reception of a mass to be removed from the abdominal cavity and collapsible or shrinkable from its expanded state. The body mass removed from the body cavity can be placed/directed through the mouth of the bag into the internal space of the bag, after which the mouth of the bag is pulled using the retractor means or using a non-traumatic grasper, till the neck end of the bag comes out of the body incision fully or partly as the case may be based on the size of the tissue mass being removed. Entryway into the internal space defined by the bag gets substantially closed when the bag is pulled through, the umbilicus (lateral/vaginal) incision using the retractor means (2), up to the 'L' marking (for about 20 to 26 cm size tumor) marked at the neck for the removal of large size tissue mass; up to 'M' marking (for about 10 to 19 cm size tumor) marked at the neck for the removal of medium size tissue mass; and up to 'S' marking (up to about 8 cm size tumor) marked at the neck for the removal of small tissue mass. The shape of the bag with the special design of the neck of the safety isolation bag, also prevent the body mass from falling off once it is placed inside. Surgical instruments and accessories are introduced through the mouth directly into the enclosed internal space or through the non-return valves.

According to another embodiment under the invention, the safety isolation bag can also be used for dermoid cyst removal by attaching two 20 to 30 cm long threads (9) at both the sides of opening of the safety isolation bag as shown in FIG. 1a. This facilitates the bag to keep in open condition during the removal of dermoid cyst, so that the ovary can be brought inside the bag and perform the procedure. Thus cyst could be completely collected inside the bag and removed by morcellation and or suction.

Various steps involved in the process of removing the tissue mass from within the body cavity, making use of safety isolation bag, are shown as an exemplary embodiment under the invention.

Figure 3:
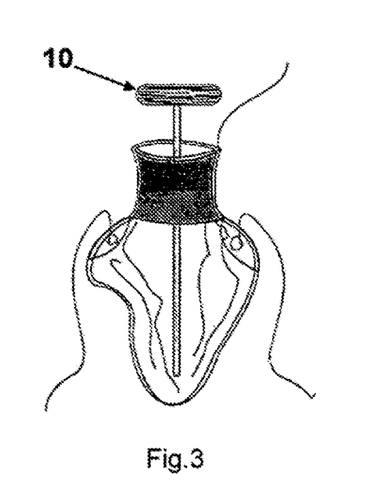
FIG. 3 shows safety isolation bag partly shrunk or in collapsed condition by inserting obturator.
Figures 4, 5:
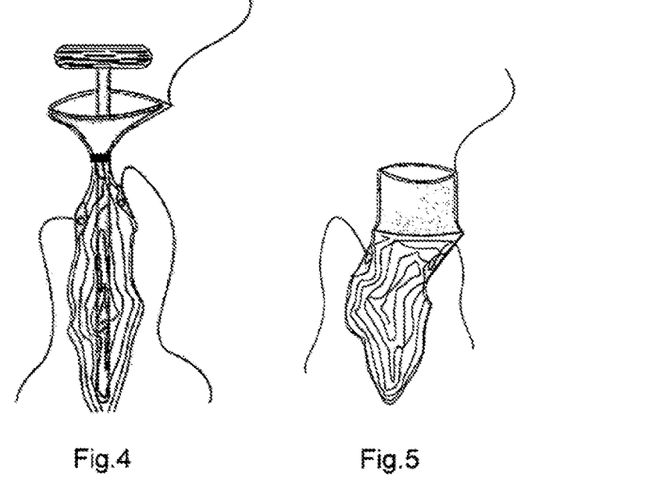
FIG. 4 shows safety isolation bag fully shrunk or in collapsed condition by inserting obturator.
FIG. 5 shows the partly collapsed bag with non-return valves.
Figure 6:
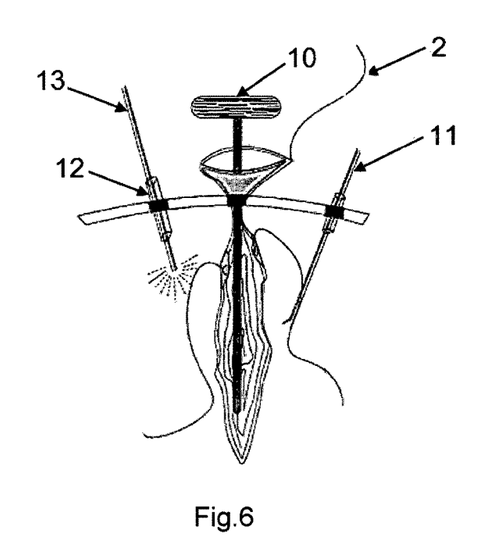
FIG. 6 shows multi-layer safety isolation bag pushed through one of the abdominal incision using the blunt obturator which is being observed by the telescope introduced through the trocar pushed through another abdominal incision.
Figure 7:
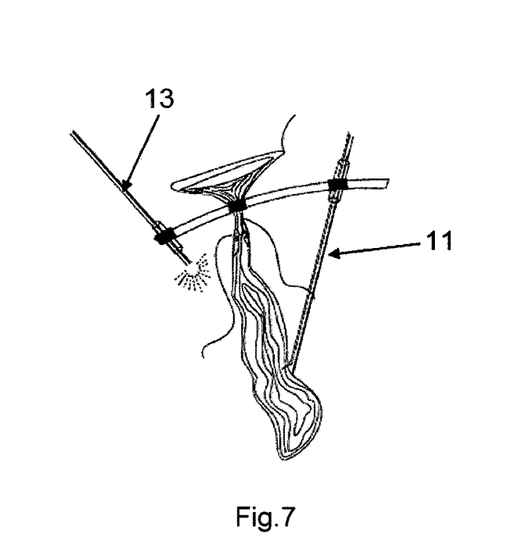
FIG. 7 shows the blunt obturator removed after pushing the multi-layer safety isolation bag with non-return valves through the abdominal incision and also shows a grasper which is used to pull the bag into the abdominal cavity.

Once doctor is ready for power morcellation the safety isolation bag is inserted into the abdominal cavity directly using the blunt tip obturator (10) by pushing the bag through the incision through which the morcellation can be performed as shown in FIG. 3 and FIG. 4. Once the safety isolation bag passes through the incision and enters in the abdominal cavity as seen in FIG. 5 the obturator is removed. Then the safety isolation bag is pulled fully into the abdominal cavity using a non traumatic grasper (11), which is monitored using the telescope (13) through the trocar (12) introduced through one of the lateral incision as shown in FIG. 6 and FIG. 7.

Figure 8:
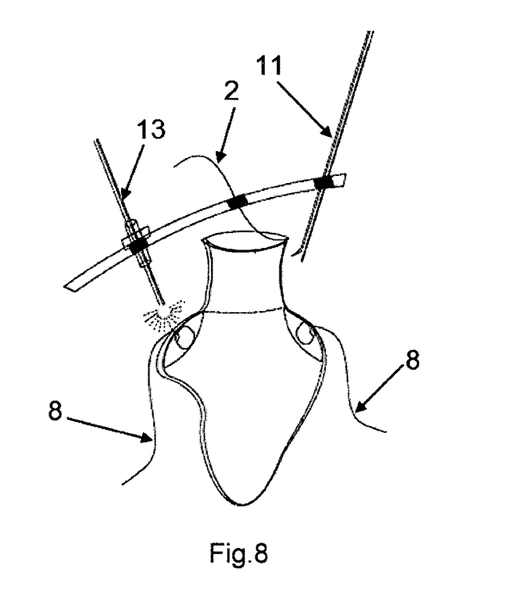
FIG. 8 shows the safety isolation bag in fully pulled condition into the abdominal cavity using a non-traumatic grasper through the lateral port while keeping the retractor means outside the abdominal cavity.

Using a non traumatic grasper (11) inserted through the lateral port, mouth of the safety isolation bag can be opened for placing the tissue mass to be removed and this procedure can be monitored using the telescope (13) inserted through one of the lateral incision as shown in FIG. 8.

Figure 9:
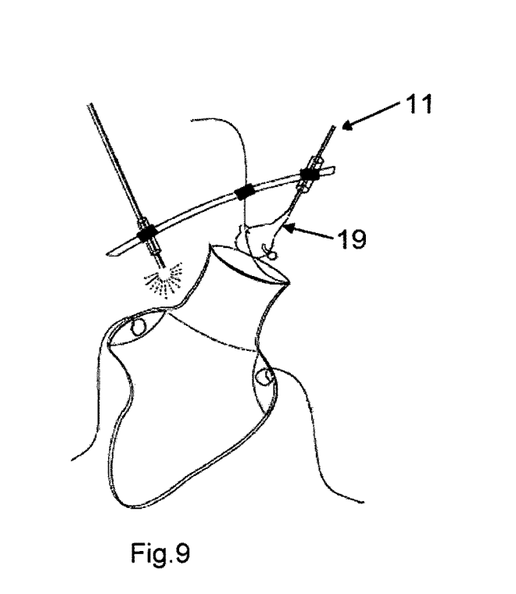
FIG. 9 shows the safety isolation bag placed inside the abdominal cavity with the mouth of the bag in opened condition for placing the surgical mass.
Figure 10:
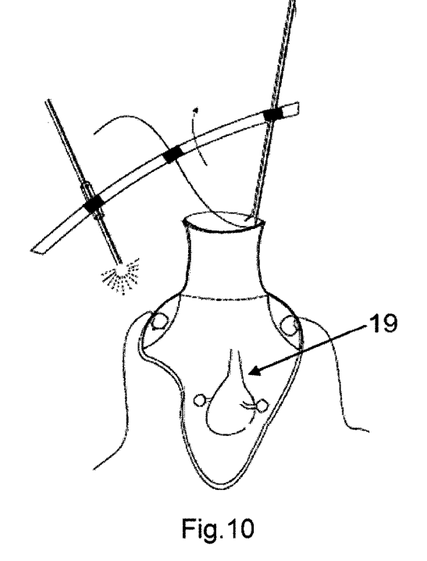
FIG. 10 shows placing the uterus (surgical mass) into the safety isolation bag using a grasper by keeping the mouth of the safety isolation bag in fully opened condition.
Figure 11:
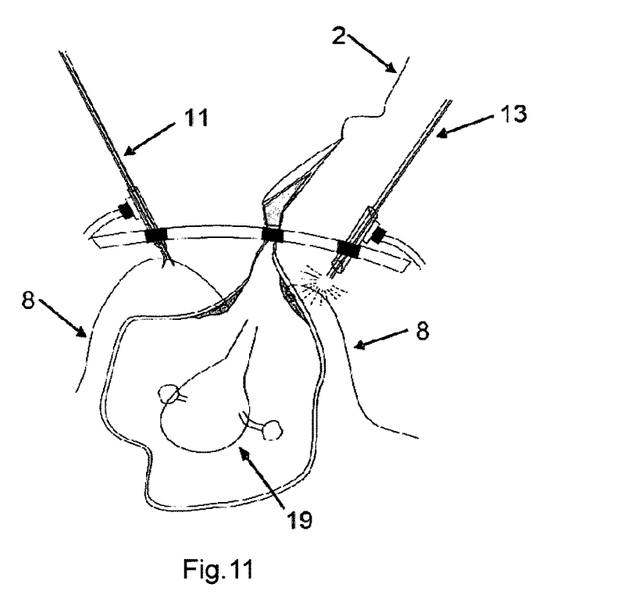
FIG. 11 shows the safety isolation bag with the uterus after placing the same into it and pulling out the neck portion of the bag by means of retractor means/grasper through the morcellation port as well as the long looped thread attached to one of the non-return valves through the lateral incision.

Once the specimens (19) are placed inside, the mouth of the safety isolation bag is pulled out through the same incision, through which the bag was inserted using the retractor means provided in the safety isolation bag or using a non-traumatic grasper till the specific marking (L, M and S) in the neck of the bag comes out of the incision depending on the size of the tissues, as shown in FIG. 9 and FIG. 10 and FIG. 11.

Figure 12:
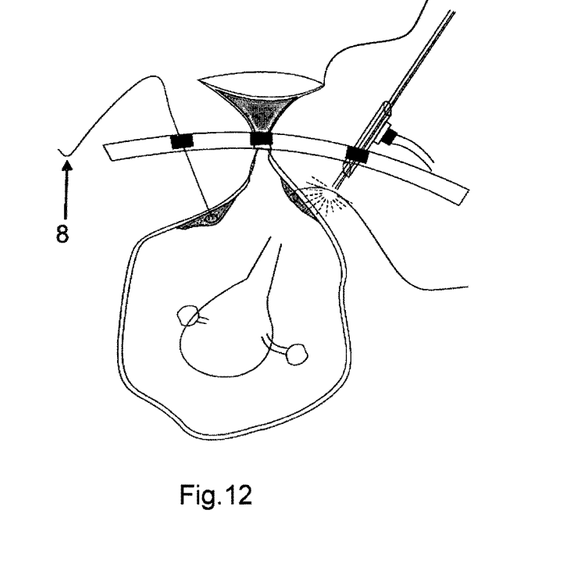
FIG. 12 shows the safety isolation bag pulled out till the neck portion comes out up to the abdominal incision matching with the markings (L, M, S) and the long loop thread attached to the non-return valve pulled out through the lateral incision.

Now the long looped thread (8) stuck to the non-return valve which is colour coded are pulled out through the primary trocar (12) passed through the lateral incision as shown in FIG. 11 and FIG. 12 by withdrawing both telescope and the trocar.

When tubular guide (8a) is provided in addition to long looped thread, as mentioned earlier according to one of the embodiment under the invention, the same can also be pulled out along the long looped thread (8) through the incision through which the trocar required to be passed. Then the closed tip of the tubular guide is cut and removed, so as to make passage for introducing the trocar.

Figure 13:
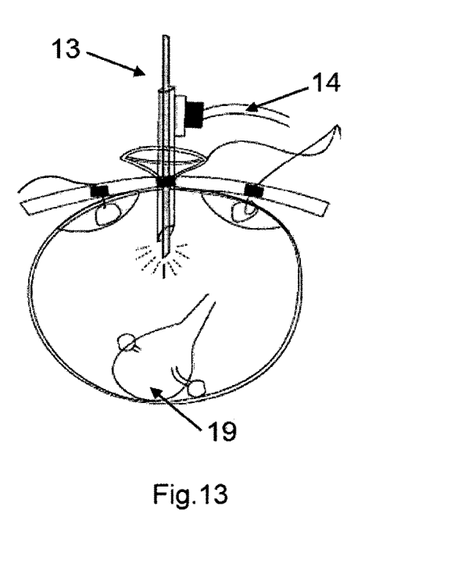
FIG. 13 shows the inflated safety isolation bag with the surgical mass is filled with gas by inserting 5 mm/10 mm trocar and visualized using the telescope passed through the trocar through the mouth of the safety isolation bag.

Now introduce one trocar (12) and telescope (13) through the mouth of the safety isolation bag and inflate the bag by passing gas through the gas tubing (14) so that complete pneumoperitoneum is created and the bag covers the abdominal cavity as shown in FIG. 13.

Figure 14:
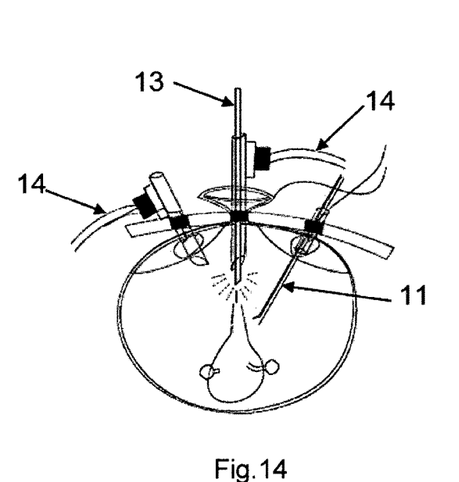
FIG. 14 shows the safety isolation bag after creating a pneumoperitoneum and covering the abdominal cavity, with telescope passed through trocar which is passed through the mouth of the bag and also seen two other trocars punctured through the non-return valves at the walls of the safety isolation bag and the long looped thread attached to the non-return valve tied to the trocar.

Once the safety isolation bag is completely filled up as visualized by the telescope inserted inside the bag, introduce one trocar (12) through the existing incision through which the long looped thread as well as the tubular guide if provided attached to the non-return valve is pulled out. Now puncturing is done at the non-return valve by the trocar by passing through the tubular guide, if provided to ensure the puncturing at the right place, while the long looped thread is pulled out through the incision. Otherwise puncturing can also be done at the non-return valve by the trocar directly. This trocar can function as the passage for the telescope (13) which is now passed through the mouth of the bag. If needed, one more trocar can be introduced through the other non-return valve of the safety isolation bag to introduce another hand instrument for the procedure as shown in FIG. 14.

Figure 15:
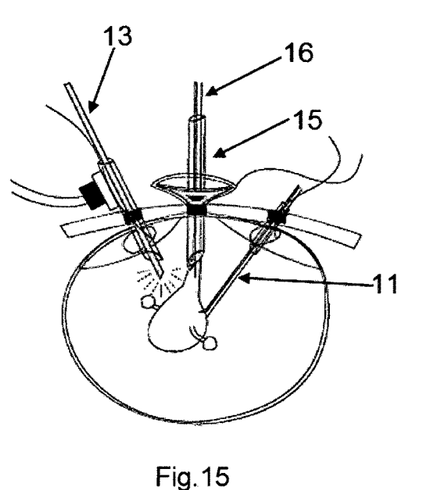
FIG. 15 shows the surgical mass (uterus) being morcellated inside the safety isolation bag which is inflated and covering the abdominal cavity and the morcellator hand piece is passed through the mouth of the bag and the trocar and telescope are passed through the non-return valve fixed to the walls of the bag and also seen another hand instrument passed through another non-return valve of the safety isolation bag.

Now the trocar and telescope can be removed from the mouth of the safety Isolation bag and the same telescope is passed through the primary trocar. The mouth opening can be used for introducing the morcellator hand piece. By visualizing by means of telescope, the morcellator hand piece (15) is introduced through the mouth opening using blunt tip obturator, and pushed into the cavity of the bag by means of spiral clockwise movement. Once all the instruments are inserted, inflate the safety isolation bag again so that the pneumoperitoneum is created and maintained throughout the procedure covering the abdominal cavity as shown in FIG. 15.

Figure 16:
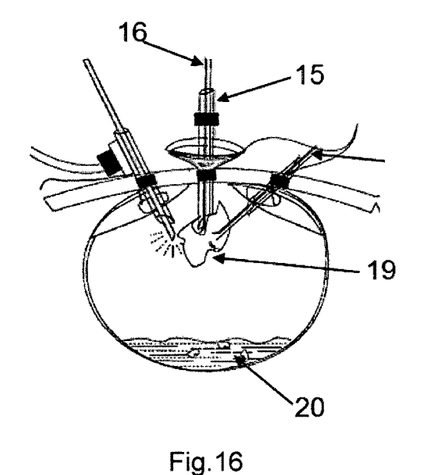
FIG. 16 shows the surgical mass (uterus) being partially morcellated inside the safety isolation bag which is inflated and covering the abdominal cavity and the small pieces of tissue and body fluids collected at the bottom of the bag during the morcellation.
Figure 17:
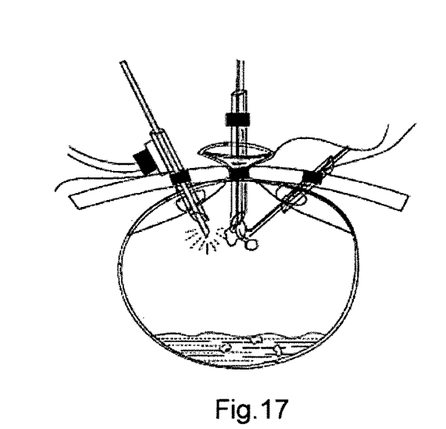
FIG. 17 shows the surgical mass (uterus) being almost morcellated inside the safety isolation bag which is inflated and covering the abdominal cavity as a pneumoperitoneum using multiple ports/multiple instruments and the small pieces of tissue and body fluids are collected at the bottom of the bag while morcellation.
Figure 18:
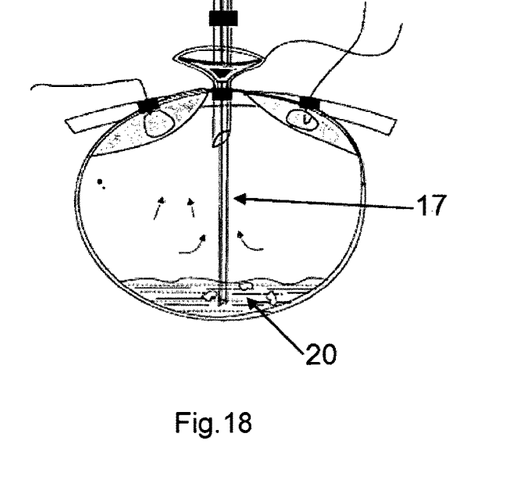
FIG. 18 shows some small tissue pieces and body fluid/blood collected inside the safety isolation bag which is being removed by the suction apparatus passed through the morcellator hand piece after the completion of morcellation (Other instruments shown in FIG. 17 is already withdrawn).

Once the blunt obturator is removed from the morcellator hand piece, a tenaculam (16) is passed through the hand piece lumen. By holding the specimen, morcellation is performed within the pneumoperitoneum created by the safety isolation bag as shown in FIG. 16. Once the morcellation is completed and the tissues are extracted, the trocars are removed from the non-return valves as shown in FIG. 17. Tenaculam (16) from the morcellator hand piece (18) is taken out and all body fluids and small tissue pieces (19) from the safety isolation bag is removed using a suction irrigation apparatus (17), which is passed through the same morcellator hand piece.

Figure 19:
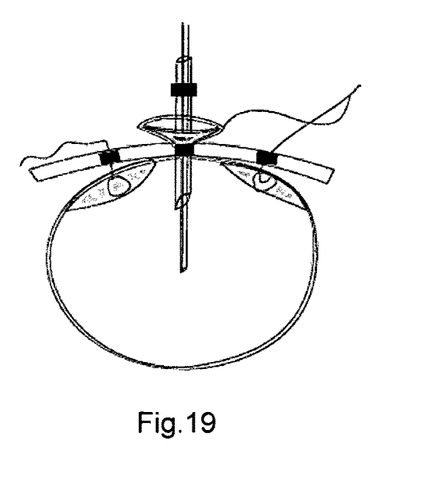
FIG. 19 shows the safety isolation bag after emptying the small tissue pieces and blood collected using the suction apparatus passed through the morcellator hand piece.
Figure 20:
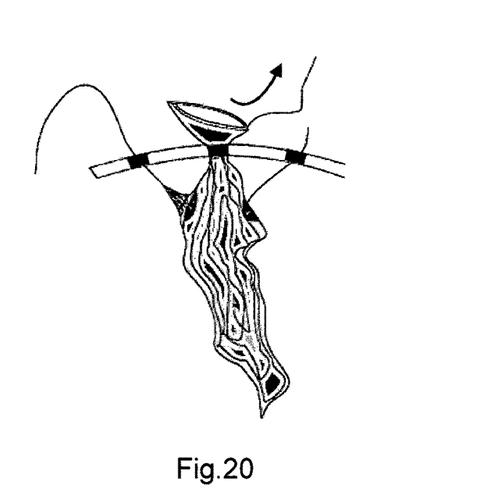
FIG. 20 shows deflated safety isolation bag with the puncture hole closed by tightly pulling the long looped thread, (after removing the trocar and morcellator hand piece) being pulled out completely outside the patient's body by the retractor means.

Safety isolation bag is deflated fully by using the suction apparatus, which is passed through the morcellator hand piece and once the device is fully deflated, the morcellator hand piece as well as the safety isolation bag is pulled out as shown in FIG. 19 and FIG. 20 after closing the puncture hole by tightly pulling the long looped thread.

A method of employing safety isolation bag comprises of the following steps.

Step-1: Widen the umbilicus incision (supra-umbilicus incision, lateral incision/vaginal incision) 12 to 15 cm or as per the convenience of the surgeon for the size of the morcellator is being used. Once it is ready for the removal of the specimen using the power morcellation, insert the safety isolation bag to the abdominal cavity directly by pushing the bag using the blunt obturator through the widened incision. Pull the safety isolation bag fully into the abdominal cavity using a non-traumatic grasper through the lateral port. Remove the obturator while pulling the safety isolation bag into the abdominal cavity using the non-traumatic grasper, keeping the retractor means outside the incision/body while it is being visualized by means of the telescope passed through the trocar introduced in one of the lateral incision.

Step-2: Open the mouth of the bag using a non-traumatic grasper through the lateral port and place the tissue specimens to be removed inside the safety isolation bag which is being monitored by the telescope.

Step-3: Pull the mouth of the safety isolation bag out through the same incision through which the bag was inserted using the retractor means provided in the safety isolation bag or using a non-traumatic grasper till the specific marking (L, M and S) in the neck of the bag comes out of the incision depending on the size of the tissues.

Step-4: Pull out the long looped thread stuck to the non-return valve which is colour coded, through the incision through which the primary trocar has to be passed. If the non return valve is attached with tubular guide in addition to long looped thread according to another embodiment under the invention, long looped thread as well as tubular guide stuck to the non-return valve is pulled out, through the incision through which the primary trocar required to be passed.

Step-5: Introduce one trocar and telescope through the mouth of the safety isolation bag and inflate the safety isolation bag through gas tubing connected to the trocar which is passed through the mouth of the bag so that the complete pneumoperitoneum is created and the abdominal cavity is covered fully with the safety isolation bag. The same can be visualized and monitored through the telescope connected to the monitor screen.

Step-6: Once the safety isolation bag is completely filled up by visualizing inside the bag, introduce one trocar through the existing incision through which the long looped thread attached to the non-return valve was pulled out and puncture at the non-return valve. If required, use another hand instrument for the procedure. Then introduce another trocar into the other non-return valve which is at the upper wall of the safety isolation bag.

In case tubular guide is provided, according to yet another embodiment under the invention, cut the closed tip of the tubular guide, and introduce one trocar through the existing incision through which the long looped thread attached to the non-return valve was pulled out and puncture at the non-return valve by passing through the tubular guide. Then introduce another trocar if needed by passing it through the tubular guide and puncture at the other non-return valve as done earlier.

Step-7: Remove the trocar and telescope which was inserted through the mouth of the safety isolation bag and pass the telescope through the primary trocar. This opening can be used for introducing the morcellator hand piece. Introduce the morcellator hand piece (cutter blade hand instrument) using blunt tip obturator and push it into the cavity of the bag using a spiral clockwise inward movement, while it is visualized through the telescope passed through the trocar and connected to the monitor screen;

Step-8: Now remove the blunt obturator from the morcellator hand piece and pass a tenaculam through the hand piece lumen and hold the specimen and perform the morcellation within the pneumoperitoneum created by the safety isolation bag. Once the morcellation is completed and the tissue mass is extracted, remove the trocars from the non-return valves/from the walls of the safety isolation bag.

Step-9: Take out the tenaculam from the morcellator hand piece, once the tissues are extracted. Remove all body fluids and small tissue pieces from the bag using a suction irrigation apparatus which is passed through the same morcellator hand piece and deflate the safety isolation bag fully by using the same suction apparatus. Pull out the morcellator hand piece and the bag together, once the safety isolation bag is fully deflated after closing the puncture hole by tightly pulling the long looped thread.

Main advantages of using the safety isolation bag according the present invention are as under.

(i) Use of safety isolation bag for intra-abdominal, endoscopic procedures, power morcellation and vaginal morcellation reduces complicated steps in safe power morcellation and removal of suspicious and life threatening body masses.

(ii) Being a single enclosed procedure, safety isolation bag makes the procedure simple and safe and avoids complicated steps.

(iii) It reduces the procedure time and makes it a better option for endoscopic surgeons and the safety of patients.

(iv) With the special design of the bag, once it is inflated, the bag will get filled completely inside the abdominal cavity keeping away all organs from field of morcellation.

(v) The chances of getting accidental puncture on the safety bag while pulling out and introducing into the abdominal cavity are almost nil in case of the safety isolation bag of the present invention, compared to bags with multi openings and tails. Since the insertion procedure of my safety isolation bag is a single step procedure, it avoids all such accidental punctures.

(vi) The multi-layer construction of the safety isolation bag is a great feature which will add immense benefits of using multiple ports while surgery for easy movement of instruments, greater vision and management and control over the surgery and also the benefit of limiting the incision size for inserting Instruments.

(vii) The non-return valves with long looped thread alone or in combination with tubular guide give an added benefit of absolute gas leak free surgery with the freedom of using multiple instruments through multiple ports enabling better vision and instrument movement for, fast and better surgery with much less learning curve and procedure time.

(viii) Provision of non-return valve with long looped thread alone or in combination with tubular guide help to puncture the safety isolation bag at right position of the valve, in addition to giving enough counter pressure for puncturing to insert the trocar.

(ix) Provisions like non-return valves help not only for introducing telescope and multiple instruments but also for easy movement of instruments during the procedure and inflating the bag to create pneumoperitoneum as well as to allow the surgeon to introduce and use the required apparatus (trocar, telescope, morcellation/cutting instrument, suction apparatus) at specific places for power morcellation and extraction of suspicious malignant body mass without using any additional accessories.

x) By pulling the long looped thread tightly after the procedure is done, the puncture hole gets closed completely to prevent any leakage of body fluid or tissues. That way it significantly reduces the procedural steps, chances of spillage and time.

(xi) The same safety isolation bag provided with two 20 to 30 cm long threads attached at both the sides of opening of the Safety Isolation Bag can be used for dermoid cyst removal from the ovary.

I have brought out the novel features of the invention by explaining some of the preferred embodiments under the invention, enabling those skilled in the art to understand and visualize my invention. It is also to be understood that the invention is not limited in its application to the details set forth in the above description or as illustrated in the drawings. Although the invention has been described in considerable detail with reference to certain preferred embodiments thereof, various changes and modifications can be made without departing from the spirit and scope of the invention as described herein above and as defined by the appended claims.

I claim:

1. A safety isolation bag, that is capable of use as a pneumoperitoneum device for intra-abdominal endoscopic procedures, power morcellation and vaginal morcellation for facilitating a safe removal of a surgical specimen or a body mass from within the abdominal cavity or from anywhere in the body, the safety isolation bag comprising: an expandable and collapsible enclosed internal space or cavity (5) having a neck portion (4) with a mouth (3) or a wide opening and the neck portion (4) is provided with markings to indicate how far the safety isolation bag is to be pulled out from an incision, wherein the markings include at least color coding, and the safety isolation bag is made of one or more layers, is leak proof, and is provided with one or more non-return valves (6) on one layer of the one or more layers for introducing surgical instruments and accessories into the enclosed internal space or cavity (5), each non-return valve of the one or more non-return valves (6) is provided with a looped thread (8) for giving counter pressure by pulling the looped thread (8) and facilitating puncture of the one or more non-retune valves (6), wherein the mouth (3) or wide opening of the safety isolation bag is kept in an open position by a flexible retainer ring (7) embedded at an upper circumferential portion of the mouth (3) or wide opening, and a periphery of the mouth (3) or wide opening is attached to a retractor (2) for facilitating pulling out the safety isolation bag through the incision.

2. The safety isolation bag as claimed in claim 1, further comprising one or more tubular guides (8a) of about 2 to 5 cm diameter with a length up to 20 cm, wherein each of the one or more tubular guides (8a) are attached in a sealing manner to each of the one or more non- return valves (6) respectively in such a way that each of the looped threads (8) are outside of the one or more tubular guides (8a).

3. The safety isolation bag as claimed in claim 1, wherein the markings further include: a) 'L' for the removal of the surgical specimen or body mass of large size of about 20 to 26 cm; b) 'M' for the removal of the surgical specimen or body mass of medium size tissue mass of about 10 to 19 cm; and c) 'S' for the removal of the surgical specimen or body mass of small size of about 9 cm and below.

4. The safety isolation bag as claimed in claim 1, wherein the one or more non- return valves (6) are gas leak proof when punctured with trocars or other surgical instruments; the one or more non-return valves (6) are formed by welding with the safety isolation bag at an earmarked portion on the one layer of the one or more layers.

5. The safety isolation bag as claimed in claim 1, wherein the safety isolation bas is capable of preventing leakage if the safety isolation bag is inflated in the abdominal cavity as a pneumoperitoneum and will retain gas if the one or more non-return valves (6) are penetrated with hand instruments.

6. The safety isolation bag as claimed in claim 1, wherein the safety isolation bag is attached to two 20 to 30 cm long threads (9) at the mouth (3) or wide opening, wherein the two 20 to 30 cm long threads facilitate keeping the safety isolation bag open during the removal of the surgical specimen or body mass.

7. The safety isolation bag as claimed in claim 1, wherein the safety isolation bag is kept in the open position with the flexible retainer ring (7) and the flexible retainer ring (7) is used to close the safety isolation bag after the surgical specimen or body mass is inserted inside the safety isolation bag.

8. The safety isolation bag as claimed in claim 1, wherein the safety isolation bag and the one or more non-return valves (6) are made up of a material is-selected from the group consisting of polyolefin, polyethylene terephthalate, polybutylene terephthalate, polyvinyl chloride, ionomer, polyurethane, nylon, polycarbonate, acrylic, ethylene vinyl acetate copolymer, polyvinylidene fluoride, low density poly ethylene, poly urethane, poly propylene and blends thereof, and wherein each looped thread (8) is made of cotton, nylon or any other polymeric material.

9. A method of employing safety isolation bag as claimed in claim 1, said method comprising the steps of:
   a) inserting the safety isolation bag into the abdominal cavity directly using a blunt obturator (10), wherein the blunt obturator (10) is first placed inside the safety isolation bag, and the safety isolation bag is rolled tightly on the blunt obturator (10), the rolled safety isolation bag is pushed into the abdominal cavity through the incision;
   b) removing the blunt obturator (10) once the safety isolation bag is inserted into the abdominal cavity, and pulling the safety isolation bag fully into the abdominal cavity using a non-traumatic grasper (11) through a lateral port or lateral incision, keeping the retractor (2) outside the lateral port or lateral incision, while being observed through a telescope (13), already inserted at a primary port;

c) opening the mouth (3) or wide opening using the non-traumatic grasper (11) through the lateral port or lateral incision and placing the surgical specimen or body mass to be removed inside the safety isolation bag;
d) pulling out the mouth (3) or wide opening through the lateral port or lateral incision using the retractor (2) or the non-traumatic grasper (11) until the markings come out of the lateral port or lateral incision;
e) pulling out at least one looped thread (8) by the non-traumatic grasper (11) through a trocar (12);
f) inflating the safety isolation bag through a gas pipe (14) connected to the trocar (12) so that a complete pneumoperitoneum is created covering the abdominal cavity which is monitored using the telescope (13);
g) pulling the at least one looped thread (8) to give a counter pressure and puncturing a first of the one or more non-return valves (6) with the trocar (12) and introducing the trocar (12) into the safety isolation bag while being visualized through the telescope 13 on a monitor screen;
h) introducing a second trocar, if required, through a second of the one or more non-return valves (6) while being visualized through the telescope (13) and introducing a hand instrument for procedural support, while having an internal view of the safety isolation bag through the telescope (13);
i) tying the at least one looped thread to the trocar (12) after the trocar (12) is introduced into the safety isolation bag to prevent accidental slippage of the safety isolation bag from the trocar (12) during a morcellation procedure;
j) inflating the safety isolation bag again through the gas pipe (14);
k) visualizing and monitoring inside of the safety isolation bag, through the telescope 13 on the monitor screen;
l) introducing a morcellator hand piece (15) through the mouth (3) or wide opening into the safety isolation bag using a second blunt tip obturator with a spiral inward movement;
m) removing the second blunt tip obturator from the morcellator hand piece (15), inserting a cutter blade into the morcellator hand piece (15), passing a tenaculam (16) through a lumen of the cutter blade, holding the surgical specimen or body mass with the tenaculam (16), and performing the morcellation procedure within the complete pneumoperitoneum of the safety isolation bag;
n) extracting the surgical specimen or body mass through the lumen of the cutter blade after completion of the morcellation procedure, taking out the tenaculam (16) and removing fluid and leftover small tissue pieces using a suction irrigation apparatus (17) which is passed through the morcellator hand piece (15);
o) deflating the safety isolation bag by using the suction irrigation apparatus (17);
p) removing the trocar (12) after untying the at least one looped thread tied to the trocar and pulling the at least one looped thread tightly so that a puncture hole is closed, and then pulling out the safety isolation bag by pulling out the morcellator hand piece (15) and the safety isolation bag together by holding onto the mouth (3) or wide opening of the safety isolation bag.

10. The method of employing safety isolation bag as claimed in claim 9, wherein in step e) pulling out a tubular guide (8a) along with the at least one looped thread (8).

* * * * *